United States Patent [19]

Saporito, Jr.

[11] 4,085,046

[45] Apr. 18, 1978

[54] RENAL DIALYSIS CONCENTRATE DELIVERY SYSTEM

[76] Inventor: Thomas J. Saporito, Jr., 6060 Forest Hills Blvd., West Palm Beach, Fla. 33406

[21] Appl. No.: 714,601

[22] Filed: Aug. 16, 1976

[51] Int. Cl.² .......................................... B01D 31/00
[52] U.S. Cl. ................................. 210/90; 210/96 M; 210/321 B
[58] Field of Search ................. 210/321 B, 22, 96 M, 210/90; 137/93, 99

[56] References Cited

U.S. PATENT DOCUMENTS

| 3,605,783 | 9/1971 | Pecker et al. | 137/93 |
| 3,722,680 | 3/1973 | Smith | 210/321 B |
| 3,744,636 | 7/1973 | Commarmot | 210/321 B |

OTHER PUBLICATIONS

Dialung, from Trans. Amer. Soc. Artif. Int. Organs, 1964, p. 125.

*Primary Examiner*—Frank A. Spear, Jr.
*Attorney, Agent, or Firm*—Arnold B. Silverman

[57] ABSTRACT

A renal dialysis concentrate delivery system comprising at least two renal dialysis concentrate reservoirs, first supply valve means and supply conduit means. First supply conduit means connecting a first concentrate reservoir to the first supply valve means. Second supply conduit means connecting a second concentrate reservoir to the first supply valve means. Concentrate pump means operatively associated with the supply conduit means. Conduit means for transporting the concentrate toward a renal dialysis machine. Return conduit means for returning concentrate to the concentrate reservoirs. The first supply valve means may be a three-way valve.

The return conduit means preferably includes a second three-way valve. Valve control means coordinate the positioning of the three-way valves so as to provide a first position wherein both valves are in communication with a first concentrate reservoir, and a second position wherein both valves are in communication with a second concentrate reservoir.

Means for determining when a concentrate reservoir is empty or approaching being empty may be provided. Such means may take the form of a pressure monitor in the supply conduit means and responsive signal generating means. Alternatively, such means may take the form of an air detector and responsive signal means.

30 Claims, 10 Drawing Figures

RENAL DIALYSIS CONCENTRATE DELIVERY SYSTEM

BACKGROUND OF THE INVENTION

1. Field of the Invention

This invention relates to automated means for supplying renal dialysis concentrate to renal dialysis machines, and, more specifically, this invention is related to equipment for supplying a number of renal dialysis machines with concentrate in proper quantity from a remote location.

2. Description of the Prior Art

In general, in renal dialysis work, a dialysis machine is connected to the patient in such fashion that blood from the patient circulates through the machine and is cleansed through indirect exposure with a water solution of a renal dialysis concentrate. It is critical to the well being of renal dialysis patients that a continuous and effective supply of renal dialysis concentrate is provided. In general, a sink is provided adjacent to the renal dialysis machine, which, in turn, is adjacent to the patient. The sink provides water for a mixture in specific quantities with the renal dialysis concentrate and a drain for disposal of waste material emerging from the renal dialysis machine.

As the manner in which the dialysis concentrate is mixed with water and processed in the renal dialysis machine forms no part of the present invention, per se, and is known to those skilled in the art, an extensive discussion of this equipment need not be presented herein. Examples of United States patents which discuss precisely controlled mixture of the dialysis concentrate with water, temperature control, sterilization, conductivity control and pressure control, are 3,508,656; 3,528,550; 3,601,255; 3,744,636 and 3,878,095. As will be appreicated from the description which follows, the present invention places primary emphasis upon delivery of the dialysis concentrate to the dialysis machine as distinguished from processing within the dialysis machine.

In a commonly employed known approach to renal dialysis the liquid concentrate is provided in five-gallon containers. The containers, which are positioned immediately adjacent to the renal dialysis machine, must be replaced after a patient's use. The five-gallon concentrate-filled containers are very heavy and quite bulky for an individual, such as a female nurse, to handle. In spite of this difficulty, coupled with the regular need for dialysis treatment by a large number of kidney patients, such an approach remains a standard approach to concentrate supply.

There remains, therefore, a present need for equipment to provide automated and reliable delivery of dialysis concentrate without involving burdensome delivery of the individual containers of concentrate to each dialysis machine.

SUMMARY OF THE INVENTION

The present invention has met the above-described need by providing an automated remotely positioned means for deliverying dialysis concentrate to a number of dialysis machines simultaneously. This system may conveniently employ two or more concentrate reservoirs containing fifty or more gallons of concentrate which may be disposed at a position remote with respect to the machines.

In general, the system provides for at least two renal dialysis concentrate reservoirs and supply conduit means for delivery of the concentrate to the renal dialysis machines. Return conduit means are provided for returning concentrate to the reservoirs when a predetermined pressure is exceeded in the supply system. Where two reservoirs are employed, a multiple position valve is placed in the supply conduit and a multiple position valve is placed in the return conduit. These valves have a first position wherein supply and return conduits are in communication with a first reservoir, and a second position wherein supply and return conduits are in communication with a second reservoir. A pump is provided in operative relationship with the supply conduit. In one embodiment, a first container, which may be a vacuum type jar or other vessel, is in communication with the pump. The vacuum container or other suitable vessel is also in communication with the return conduit which may preferably contain a second vessel and a relief valve set to open at a predetermined pressure in order to permit return of concentrate to one of the reservoirs. Dialysis concentrate emerging from the first vacuum container or vessel may preferably be connected to a header which, through a number of feeder tubes, is each connected to outlets for discharge of concentrate to dialysis units. The feeder tubes are each preferably provided with a check valve in order to resist the flow of concentrate through the particular feeder when it is not connected to a dialysis machine.

Means are preferably provided for indicating when a reservoir is empty. One form of such means is a pressure monitor provided in the supply conduit so as to emit a signal when the pressure in the conduit drops below a predetermined level. An alternate approach is to provide an air detector which emits a signal when air begins to flow therethrough in predetermined quantities.

The liquid concentrate passing through the supply system preferably passes under the influence of a combination of pressure established by the pump, the suction drawn by the dialysis machine or machines which are in operation, and connected to the feeder tubes, and, where practical, also under the influence of gravity. It will be appreciated that for some installations primary or sole reliance may be placed upon one or more, but less than all three, of these transport means.

It is an object of the present invention to provide an economic, reliable, automated means for deliverying dialysis concentrate to one or more dialysis machines from a remote location.

It is another object of this invention to eliminate burdensome transport of individual dialysis concentrate containers to each dialysis machine.

It is yet another object of the present invention to provide such an automated dialysis concentrate delivery system wherein safety means are provided in order to monitor the depletion of the concentrate supply in a particular reservoir and to return concentrate to a reservoir when the pressure in the system exceeds a predetermined level.

These and other objects of the invention will be more fully understood from the following description of the invention on reference to the illustrations appended hereto.

DESCRIPTION OF THE PREFERRED EMBODIMENTS

Figure 1:
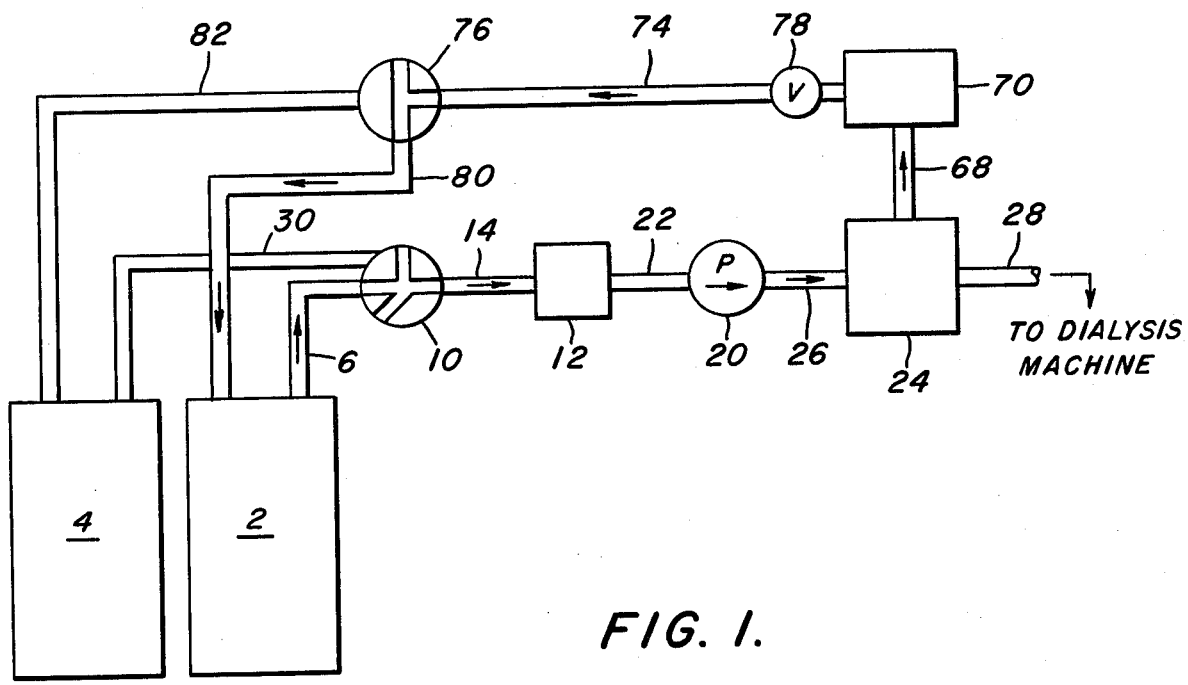
FIG. 1 is a schematic illustration of a portion of the fluid handling system of the present invention.

Referring now to FIG. 1, there is shown a pair of large liquid dialysis concentrate reservoirs 2, 4 which may conveniently be on the order of fifty-gallon capacity. A first fluid supply conduit 6 is in communication with reservoir 2 and supply valve 10. As will be described hereinafter, supply valve 10 is preferably a three-way solenoid valve. A pressure monitor 12 is in communication with valve 10 through supply conduit 14. The pressure monitor 12, which forms no part of the invention, per se, may conveniently be any conventional type which emits a signal when the concentrate pressure drops below a predetermined level. Among the suitable types of pressure monitors, for example, are those wherein fluid pressure deforms a diaphragm to deflect a meter and those wherein a photocell emits a signal responsive to depletion of fluid in the conduit. The pressure monitor 12 is set to emit a signal when the fluid dialysis concentrate pressure within the supply system is reduced beyond a predetermined level so as to indicate that the reservoir supplying the concentrate is either empty or is becoming empty so that the supply means may be switched into communication with a full reservoir. Pump 20 is preferably of the occlusion variety in order to minimize the likelihood that air or gas bubbles will be delivered with the concentrate. Pump 20 also preferably has a variable speed control. Fluid conduit 22 operatively connects pressure monitor 12 with pump 20. Container 24, which may be a vacuum jar, receives dialysis concentrate under pressure from pump 20 through supply conduit 26. In normal operation, the concentrate emerges from container 24 through supply conduit 28 on its way to the dialysis machines as will be described below.

Figure 4:
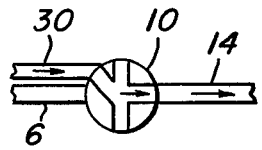
FIG. 4 is a schematic illustration of a three-way valve in the return conduit means of the present invention.

In the form shown, it is noted that concentrate reservoir 4 is in communication with valve 10 by means of the supply conduit 30. In the valve position illustrated in FIG. 1, the valve 10 is in a first position which permits flow from reservoir 2 through conduit 6 to the valve 10 to the remainder of the supply system, and supply from reservoir 4 is not permitted. Referring to FIG. 4, the valve 10 is shown in a second position which permits flow from reservoir 4 through supply conduit 30 through valve 10 to the remainder of the system through supply conduit 14. Supply from reservoir 2 through supply conduit 6 is precluded. The manner in which three-way valve 10 is moved from one position to the other will be described below. This switching will generally be accomplished when it is desired to switch from an empty reservoir to one which contains a supply of the dialysis concentrate.

Figure 2:
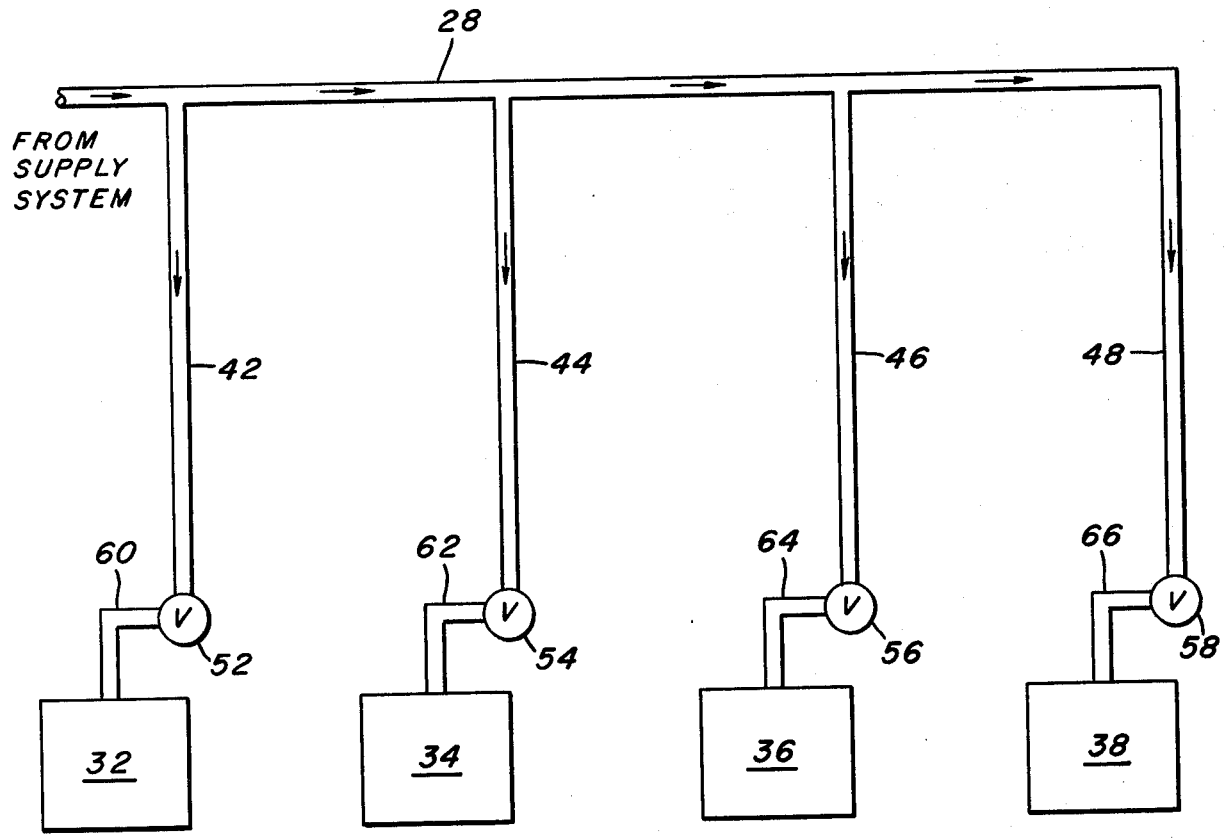
FIG. 2 is a schematic illustration of a concentrate supply header, the supply tubes and related delivery items.

Referring now to FIG. 2, it is seen that the supply conduit 28 which emerges from container 24 serves as a header in distributing dialysis concentrate to a number of dialysis machines 32, 34, 36, 38. It will be appreciated that for convenience of illustration the use of the system in combination with four dialysis machines has been illustrated, but a greater or lesser number may be supplied should such an arrangement be desirable. A number of supply tubes 42, 44, 46, 48 have their upper ends in communication with supply header 28 and receive concentrate therefrom. At the lower end of supply tubes 42, 44, 46, 48 are valves 52, 54, 56, 58, respectively. These valves when in a closed position preclude distribution of dialysis concentrate from the particular supply tubes. These valves are preferably in the form of check valves which are adapted to resist emergence of dialysis fluid in their normal position but may be displaced by a suitable connector so as to permit flow through a tube into the associated dialysis machine. Such tubes have schematically been indicated by the reference numbers 60, 62, 64, 66, respectively.

It will be appreciated that when it is desirable to initiate the use of a particular dialysis machine, all that need be done is that the fluid connection be completed at the valve associated with the supply tube which would be employed. For example, if one were to initiate use of dialysis machine 32, one need merely effect the connection of tube 60 with supply tube 42 with valve 52 being in an open position.

Before considering other detailed structural features of the system, it is believed desirable to discuss the means of transport of the dialysis concentrate, within the sytem. A prime means of concentrate delivery is the pressure generated by pump 20. In addition, a dialysis machine in operation creates a suction which will tend to draw the concentrate into the machine. Finally, in the form illustrated, the header 28 is at a higher elevation that the dialysis machines 32, 34, 36, 38, and gravity will assist with the delivery of concentrate to the machine. If desired, primary reliance may be placed on one or two of these contributing features. Allowance for the contribution of gravity and/or suction can permit increased economies through reduction of pump size. It is important, however, that the pressure be adequate to provide effective delivery of the needed quantities of concentrate even when all of the dialysis machines are operating simultaneously.

As situations may arise where the relationship between the pressure in the concentrate and the rate at which the concentrate is being employed by the dialysis machine is such that pressure may build up to an undesirably high level in the system, it is preferred to provide a return conduit system. In a preferred form of the invention, when a predetermined pressure is exceeded, dialysis concentrate will be returned to a supply reservoir until the pressure within the supply system drops below the predetermined level. Referring again to FIG. 1, it is noted that return conduit 68 connects container 24 with container 70. Return conduit 74 connects container 70 with valve 76. Valve 76 is preferably a three-way solenoid valve and may be generally similar to valve 10 in respect of function, although different internal geometry may be provided if desired or required. Valve 78 in the form shown in illustrated as being positioned within return conduit 74, but, if desired, it could well be placed within container 70, container 24 or return conduit 68. It is preferably a relief valve adapted to open when a predetermined pressure has been exceeded thereby permitting dialysis concentrate to flow toward valve 76.

Figure 3:
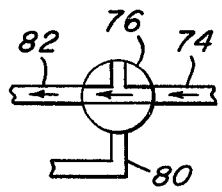
FIG. 3 is a schematic illustration of a three-way valve in the supply conduit means of the present invention.

In the position of valve 76 shown in FIG. 1, concentrate passing through return conduit 74 and valve 76 emerges through return conduit 80 and delivers concentrate to reservoir 2. The passage of concentrate through valve 76 to return conduit 82 and to reservoir 4 is precluded with valve 76 in the position shown. It will be appreciated, therefore, that when valves 10 and 76 are in the illustrated positions, supply of concentrate is provided by reservoir 2, and any return concentrate is returned to reservoir 2. Referring now to FIG. 3, valve 76 is shown in another position which permits flow of return concentrate through valve 76 to return conduit 82 and precludes flow through valve 76 to return conduit.

As has been indicated above, valves 10, 76 are preferably three-way solenoid valves which may conveniently assume one of two positions, each of which provides for both supply and return of dialysis concentrate from and to a particular reservoir. A convenient manner of controlling the position of valves 10, 76 is to provide an electrical means (to be described below) which will apply either a first voltage or a second voltage to the valve. The first voltage may correspond with a first position of the valves 10, 76 (FIG. 1), and the second voltage may correspond with a second position of the valves 10, 76 (FIGS. 3 and 4). For example, application of 24 AC volts may correspond to the valves 10, 76 in the first position and zero AC volts may correspond with the valves 10, 76 being in a second position. It will generally be desirable to permit manual switching from one reservoir to another after an indicator or alarm has indicated depletion of the concentrate supply in the reservoir that is in use. Regardless of whether the switching will be effected in a manual or in some automatic fashion, it is desirable to provide an indication to personnel that the change has been effected. This may conveniently be accomplished by a visual light signal and/or an audible indicator.

Figure 5:
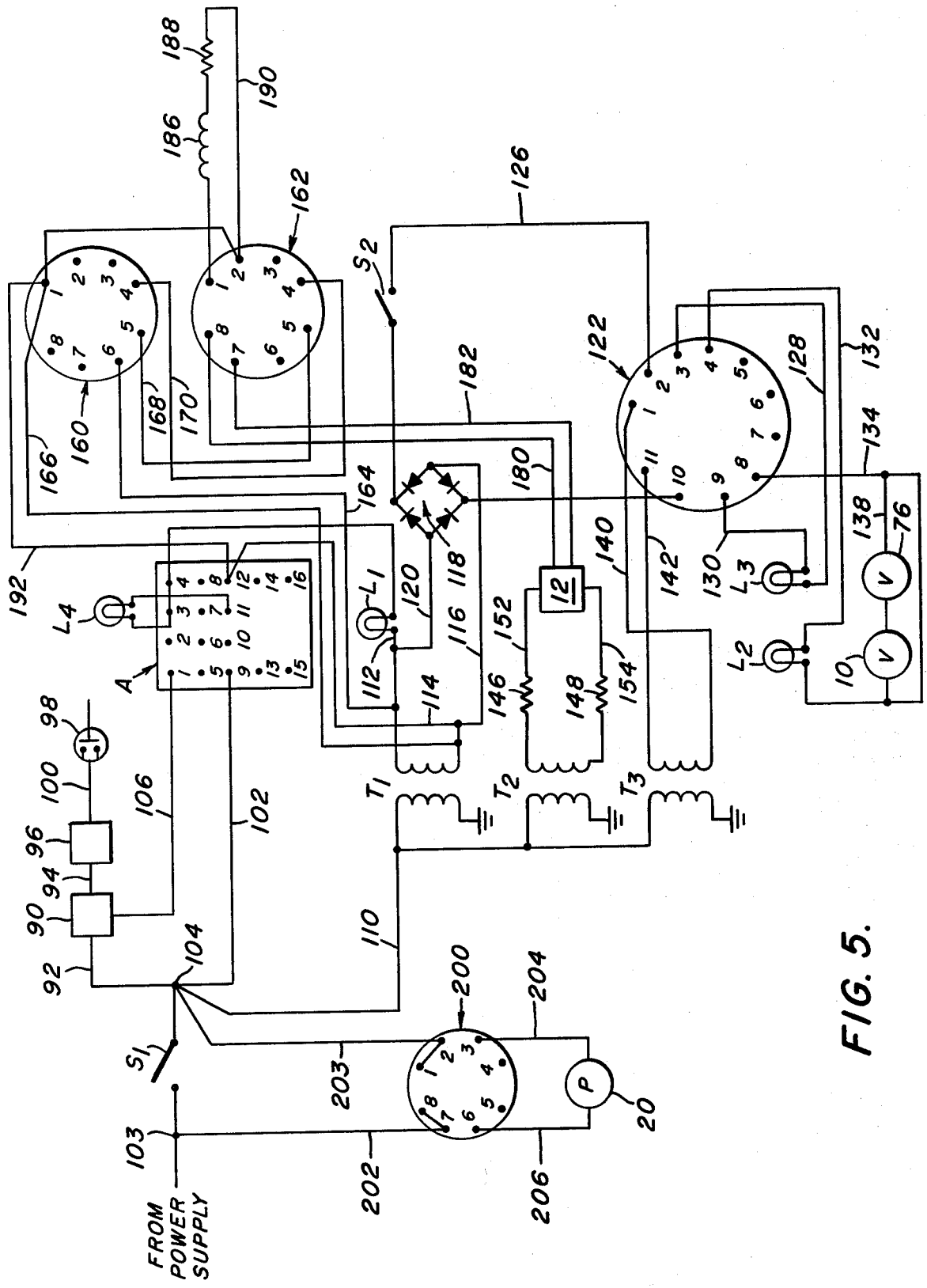
FIG. 5 is a partially schematic electrical circuit diagram showing the electrical system employed in a preferred embodiment of the present invention.

Referring now to FIG. 5, there is shown a schematic of a preferred form of electrical control system for use in the renal dialysis concentrate delivery system of the present invention. As is seen in the upper left-hand corner of FIG. 5, a power supply which may conveniently be a 115 volt AC source (not shown) is operatively connected and disconnected from the system by main switch $S_1$. Electrical lead 92 supplies the current to the audio alarm portion of this system. Battery eliminator 90 receives the 115 volt AC current and converts it into nine volt DC for supply to audio alarm 96 through lead 94. The battery eliminator may conveniently include a step-down transformer and rectifier. Audio alarm 96 is connected to mute switch 98 by means of lead 100. It is noted that lead 102 connects junction 104 with relay pin 9 of relay A. Lead 106 connects battery eliminator 90 with relay pin 1 of relay A. When main switch $S_1$ is in the open position with the system being turned off, relay A is in the closed position so that the circuit between pins 1 and 9 is complete, and the alarm circuit is also in functional position. But for the fact that current is not being received from the power supply, the audio alarm 96 would sound. When main switch $S_1$ is closed to energize the system, relay A is energized, thereby breaking the completed circuit between pins 1 and 9. In the event that the pressure monitor 12 indicates that the system pressure has been reduced below the predetermined set point, the alarm circuit would be closed in a manner to be described below, and audio alarm 96 would sound as well as alarm light $L_1$ becoming illuminated. The sounding of the alarm 96 and illumination of the light $L_1$ is designed to attract the attention of personnel responsible for maintaining the system. By manually operating mute switch 98, the audio alarm 96 is turned off. In a preferred form, mute switch 98 is such that depression will merely result in silencing of the alarm for a fixed, relatively short, period of time, such as 45 seconds, for example, after which time the audio alarm 96 will resume sounding unless the system has been taken out of the alarm state.

Shown toward the central portion of FIG. 5 are three step-down transformers $T_1$, $T_2$, $T_3$. When main switch $S_1$ is in the closed position, 115 volt Ac current will be supplied to the transformers $T_1$, $T_2$, $T_3$ by means of lead 110. $T_1$ converts the current into 24 volt AC current. Lead 112 connects light $L_1$ with pin 4 of relay A. Lead 114 is connected to pin 12 of relay A. Lead 116 connects the secondary winding of transformer $T_1$ with rectifier bridge 118. Bridge 118 converts received AC into DC. Lead 120 connects lead 112 with one contact of bridge 118. Switching relay 122 has pin 10 connected to another contact of bridge 118 by lead 124. Finally, lead 126 connects pin 2 of switching relay 122 to a contact of bridge 118. Switch $S_2$ which is positioned within lead 126 provides a manual means for switching from one reservoir 2, 4 (not shown in this view) to the other by repositioning of valves 10, 76. As was indicated in the example provided above, the valves 10, 76 are adapted to be in first position which permits flow to and from one reservoir 2, 4 when no voltage is imposed upon the valves 10, 76, and a second position when a voltage of 24 volts is imposed upon the valves 10, 76.

Lamps $L_2$, $L_3$ are designed to be illuminated when their related reservoirs 2, 4 (not shown in this view) are being employed. Thus, when valves 10, 76 are in a first position which connects the supply and return conduits with one reservoir 2, 4 one of lamps $L_2$, $L_3$ will be illuminated, and when the other reservoir 2, 4 is being employed with the valves 10, 76 in the other position, the other lamp $L_2$, $L_3$ will be illuminated. Lamp $L_3$ is connected by lead 128 with pin 3 of relay 122 and by lead 130 with pin 9 of relay 122. Lamp $L_2$ is connected by lead 132 with pin 4 of relay 122, and by lead 134 to pin 8 of relay 122. Lead 138 connects valves 10, 76 with lead 134 at two locations. With $S_2$ in one position, 24 volts DC are supplied to valves 10, 76, and they are in a first position. With $S_2$ in the other position, zero volts are imposed on the valves 10, 76, and they are in a second position. The secondary winding of transformer $T_3$ is connected to pin 1 of relay 122 through lead 140, and pin 11 of relay 122 through lead 142. In the example selected for illustration, transformer $T_3$ is a step-down transformer which provides 24 volt AC current to lamps $L_2$, $L_3$ through switching relay 122 so that one or the other lamp may be illuminated regardless of whether switch $S_2$ is in the opened or closed position.

Referring still to FIG. 5, attention is now directed to step-down transformer $T_2$ which adapted to provide 12 volts AC to pressure monitor 12. Resistor 146 is provided in lead 152 which connects the secondary winding of transformer T₂ with pressure monitor 12 and resistor 148 is provided in lead 154 which connects secondary winding of transformer T₂ with pressure monitor 12. Referring now to the upper right-hand portion of FIG. 5, there is shown power supply module 160 and sensor module 162. Power supply module 160 is energized with 24 volts AC from the secondary winding of transformer T₁ by means of lead 164 which is connected to pin 6 of power supply module 160 and lead 166 which is connected to pin 1 of power supply module 160. Sensor module 162 is energized by means of lead 168 which connects pin 5 of power supply module 160 with pin 5 of sensor module 162 and lead 170 which connects pin 4 of power supply module 160 with pin 4 of sensor module 162. Referring again to pressure monitor 12, it is seen that lead 180 connects pressure monitor 12 with pin 8 of sensor module 162, and lead 182 connects pressure monitor 12 with pin 7 of sensor module 162. When the pressure set point in pressure monitor 12 is violated by the pressure of the concentrate dropping below the set point, a signal so indicating is communicated to sensor module 162 by leads 180, 182. A signal from pin 1 of sensor module 162 passes through relay coil 186 and resistor 188 on lead 190 and then to pin 2 of sensor module 162 from which it is communicated to pin 1 of power supply module 160 and from there by means of lead 192 to pin 12 of relay A. This imposes a voltage across relay A which de-energizes the relay and closes the circuits 1-9, 3-11 and 4-12. In so doing, contact between pins 1 and 9 of relay A is completed to thereby initiate sounding of audible alarm 96. Also, contact is made between pins 4 and 12 of relay A to thereby energize the lamp L₁, and pins 3 and 4 of relay A are permanently shorted. The remote alarm indicator light L₄ is illuminated as a result of closing the circuits between pins 3 and 11. The use of remote light L₄ provides the advantage of a visual alarm at a location other than that of L₁. When the operator moves switch S₂ to the other position so that the supply of concentrate is initiated from the other reservoir and the pressure of concentrate within pressure monitor exceeds the set point, the signal from pressure monitor 12 will cease to be emitted, and the relay A will be energized to thereby open the alarm circuit and cease both the audible alarm 96 and the illumination of lamps L₁, L₄.

Referring now to the extreme left-hand portion of FIG. 5, there is shown a 115 volt relay 200 which is connected by lead 202 with the power supply through junctions 103 and 104. Lead 202 is connected to pin 7 which is shorted with pin 8 of relay 200. Lead 203 connects junction 104 with pin 2 which is shorted with pin 1. Pump 20 is connected by means of leads 204, 206 to pins 3 and 6, respectively, of relay 200. When the main switch S₁ is turned on, the pump 20 will be energized to initiate flow of concentrate.

Figure 9:
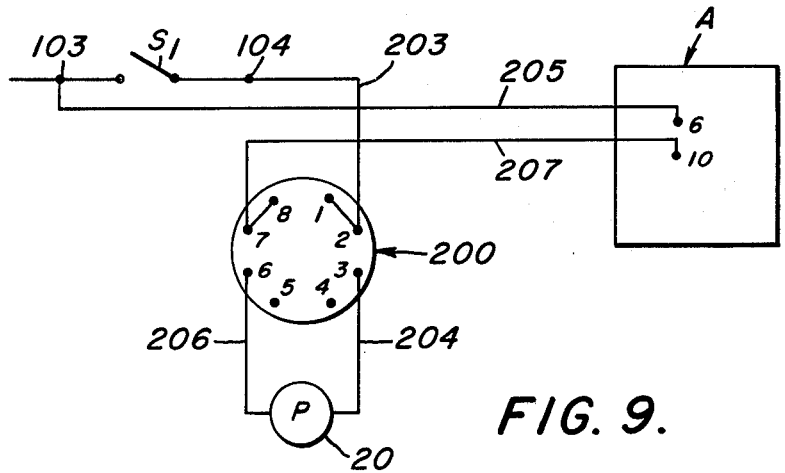
FIG. 9 is a fragmentary schematic illustration of a modified concentrate pump control circuit.

In a modified form of the invention illustrated in FIG. 9, means may be provided to shut off the pump 20 automatically in the event the system goes into an alarm state. Pump 20 remains wired to relay 200 as in FIG. 5. Pin 2 of relay 200 is connected to junction 104 by lead 203, and pin 7 of relay 200 is connected to pin 10 of relay A by lead 207. Lead 205 connects pin 6 of relay A with junction 103. In normal operation with relay A energized, circuit 6-10 is closed, and pump 20 is supplied with current. In the event that relay A is de-energized as in going into an alarm state, circuit 6-10 is automatically opened, and current flow to pump 20 is terminated. Upon cessation of alarm state, relay A is energized, thereby closing circuit 6-10 in relay A and providing current to operate pump 20.

Figure 10:
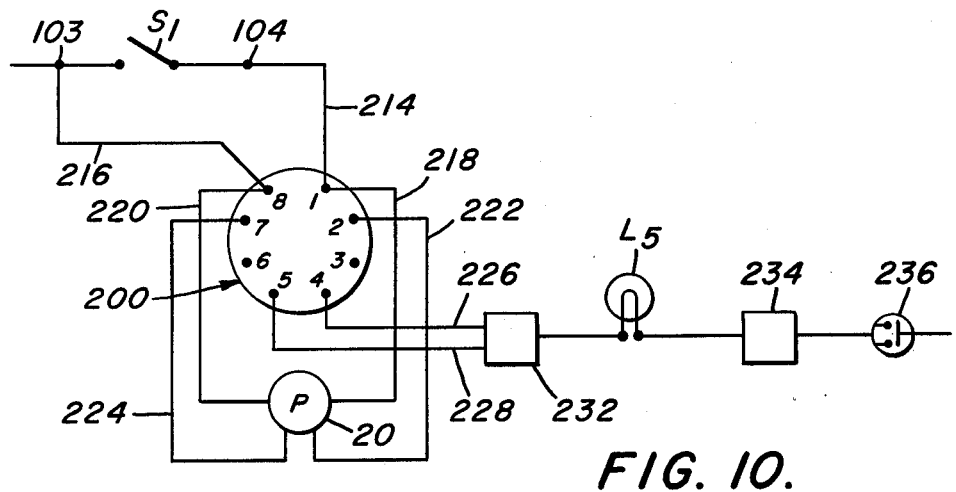
FIG. 10 is a schematic illustration of a form of pump shutoff alarm.

Referring to FIG. 10, there is shown a form of alarm system adapted to give an indication that the pump has ceased to operate. This could occur for reasons other than automatic shutoff during a general system alarm, as is shown in FIG. 9. For example, the pump fuse could be triggered to sever the circuit or the pump could merely break down. In FIG. 10, the pump 20 is energized (when switch S₁ is closed) by lead 216 which connects pin 8 of relay 200 to junction 103 and lead 214 which connects pin 1 of relay 200 to junction 104. Leads 218, 220 connect pins 1, 8, respectively, to pump 20. Leads 222, 224 connect pins 2, 7, respectively, to field winding of pump 20 which is electrically downstream of the fuse (not shown). In the event of fuse destruction or other pump failure, leads 222, 224 would no longer "see" the operating voltage across the field winding. A responsive signal is emitted along leads 226, 228 from pins 4 and 5 of relay 200 to battery eliminator 232 which may be the same as battery eliminator 90 (FIG. 5). This results in illumination of alarm lamp L₅ and initiation of output from audio alarm 234. Mute switch 236 which may be similar to switch 98 is provided to permit shut-off of audio alarm 234. The alarm 234 should be such that its output is distinguishable from that of alarm 96.

Figure 6:
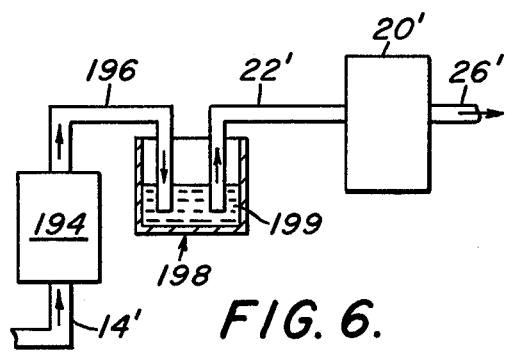
FIG. 6 is a partially schematic illustration of an air detector approach to monitoring reservoir depletion in accordance with the present invention.

Referring now to FIG. 6, an alternate form of pressure monitor which is adapted to signal exhaustion of one reservoir and the need to transfer to another will now be considered. In this version, an air bubble detector is inserted into the supply conduit. In the event that fluid flow is diminished to the point of creating a predetermined quantity of gas or air in the lines, the air bubble detector will emit a signal so indicating. In this system, supply conduit 14' introduces fluid into air bubble detector 194 with supply conduit 196 introducing the concentrate fluid into vessel 198 from which it passes through supply conduit 22' to pump 20' and emerges therefrom through conduit 26'. In this embodiment, the air bubble detector may contain a conventional photocell unit (not shown) wherein a light beam is disposed on one side of the concentrate conduit passing through air bubble detector 194 and a receiver is positioned on the other side thereof. When a continuous stream of concentrate fluid is passing through the air bubble detector, the receiver will receive a different quantity of light than when air or other gas is present in meaningful quantities in the air bubble detector. In this latter instance, the photocell will emit an electrical signal which will result in establishing an alarm state for the system in order to indicate the need to transfer to a reservoir which contains a large quantity of the concentrate. Vessel 198 is employed merely as an added convenience in order to reduce the likelihood that air will be supplied along with the concentrate. A quantity of concentrate liquid 199 is shown having an upper surface above the lower extremities of supply conduit 196, 22'.

Figure 7:
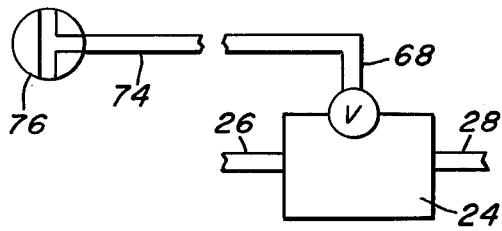
FIG. 7 illustrates a fragmentary schematic view of an alternate embodiment of the present invention.

Referring now to FIG. 7, there is shown a modified form of the invention wherein the use of container 70 has been eliminated. As is seen, a pressure relief valve V has been inserted either in line 68 or within container 24 so as to open automatically when a predetermined pressure has been exceeded so as to permit flow through conduit 68 to conduit 74 and valve 76. While the embodiment of FIG. 1 employing container 70 is preferred as it provides an additional reservoir for absorption of surging fluid in the event of a surge in pressure, the embodiment of FIG. 7 may, nevertheless, be employed advantageously in many uses.

Figure 8:
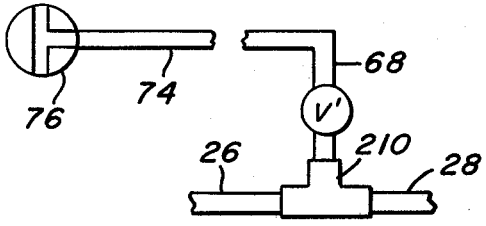
FIG. 8 is a fragmentary schematic illustration of another embodiment of the present invention.

Referring to FIG. 8, there is shown a further modified form of the invention generally similar to the embodiment of FIG. 7 except for the fact that the use of container 24 has been eliminated. In this embodiment, a T-joint 210 connects return line 68 with supply conduits 26, 28. A valve V' which is a pressure relief valve adapted to permit flow therethrough only when a predetermined pressure has been exceeded is introduced into line 68. While this embodiment is not the preferred embodiment, it may, nevertheless, be employed advantageously in numerous uses.

It will be appreciated, therefore, that the present invention has provided an economical, simple and effective means of delivering critical dialysis concentrate materials to a number of dialysis machines in a reliable fashion. All of this is accomplished without the need for personnel, such as nurses, to haul heavy and bulky individual multi-gallon drums of concentrate to each dialysis machine. Also, the present system provides safety means which insure a continuous supply of dialysis fluid from additional reservoirs when a given reservoir has been exhausted. Further, accidental explosions and other mishaps resulting from excessive pressure are eliminated as a result of the return system which has been provided. It will be appreciated that a further advantage of the invention is the ability to supply the concentrate from large reservoirs positioned in remote locations, and thereby to free the patient area of the need to provide space for individual dialysis concentrate as well as the need to transport the same through the patient areas. In effect, use of the concentrate delivery system by hospital personnel requires merely plugging in a connecting tube in order to initiate flow to a particular dialysis machine.

While for purposes of simplicity of illustration herein, reference has been made to the use of a system employing two reservoirs, it will be appreciated that a greater number of reservoirs may be employed if desired. All that is required is that either the valves 10, 76 be provided with additional positions to accommodate the additional supply and return lines or that additional valves and lines be provided, and that appropriate control means for positioning the valves be provided.

While the system is uniquely adapted to supply a larger number of dialysis machines simultaneously, it will be appreciated that four have been shown in the present disclosure solely for purposes of example, and that the invention is not limited to either a system arranged to supply solely four dialysis machines or to a system wherein all or a substantial portion of the machines to be supplied are, in fact, in operation simultaneously.

Whereas particular embodiments of the invention have been described above for purposes of illustration, it will be evident to those skilled in the art that numerous variations of the details may be made without departing from the invention as defined in the appended claims.

I claim:

1. A renal dialysis concentrate delivery system comprising:
   at least two renal dialysis concentrate reservoirs,
   first supply valve means,
   supply conduit means having first, second and third supply conduit means,
   said first supply conduit means connecting a first said concentrate reservoir to said first supply valve means,
   said second supply conduit means connecting a second said concentrate reservoir to said first supply valve means,
   said third supply conduit means for transporting said concentrate from said first supply valve means to at least one renal dialysis machine,
   said first supply valve means being a multiple position valve having a first position permitting flow of concentrate from said first concentrate reservoir through said first supply valve means, and a second position permitting flow from said second concentrate reservoir through said first supply valve means,
   a concentrate pump in said third supply conduit means, and
   return conduit means disposed downstream from said pump and connecting said third conduit means with said concentrate reservoirs.

2. The renal dialysis concentrate delivery system of claim 1 including
   pressure monitor means in communication with said third supply conduit means.

3. The renal dialysis concentrate delivery system of claim 2 including
   means responsive to said pressure monitoring system indication of concentrate pressure being below a predetermined level to initiate a signal so indicated.

4. The renal dialysis concentrate delivery system of claim 3 including
   said means responsive to said pressure monitoring system including electrical means for initiating an alarm responsive to receipt of said signal.

5. The renal dialysis concentrate delivery system of claim 4 including
   said electrical means including relay means for completing the circuit for initiating said alarm.

6. The renal dialysis concentrate delivery system of claim 5 including said alarm system having audible alarm means.

7. The renal dialysis concentrate delivery system of claim 5 including said alarm means including visual alarm means.

8. The renal dialysis concentrate delivery system of claim 5 including
   means for terminating said alarm responsive to cessation of said signal indicating concentrate pressure deficiencies.

9. The renal dialysis concentrate delivery system of claim 1, including said first supply valve means being a solenoid valve.

10. The renal dialysis concentrate delivery system of claim 1 including
    said return conduit means having first return conduit means, second return conduit means and third return conduit means,
    first return valve means operatively associated with said return conduit means for selectively permitting concentrate flow to said first and second reservoirs,
    said first return conduit means connecting said third supply conduit means with said first return valve means,
    said second return conduit means connecting said return valve means with a first said concentrate reservoir, and said third return conduit means connecting said return valve means with said second concentrate reservoir.

11. The renal dialysis concentrate delivery system of claim 10 including first container means for providing additional concentrate receiving capacity in communication with said third supply conduit means.

12. The renal dialysis concentrate delivery system of claim 11 including second container means for providing additional concentrate receiving capacity disposed within said first return conduit means.

13. The renal dialysis concentrate delivery system of claim 10 including
pressure relief valve means for permitting flow of said concentrate to said return valve means when concentrate pressure exceeds a predetermined level.

14. The renal dialysis concentrate delivery system of claim 10 including
said return valve means being a three-way valve having a first position permitting flow through said valve from said first return conduit means to said first concentrate reservoir, and a second position permitting flow through said valve from said first return conduit means to said second concentrate reservoir.

15. The renal dialysis concentrate delivery system of claim 14 including said return valve means being a solenoid valve.

16. The renal dialysis concentrate delivery system of claim 10 including
said first supply valve means and said return valve means each being three-way valves,
valve control means for placing said three-way valves in a first position in communication with one said concentrate reservoir, and a second position in communication with the other said concentrate reservoir.

17. The renal dialysis concentrate delivery system of claim 16 including
said three-way valves being solenoid valves, and
said valve control means being electrical.

18. The renal dialysis concentrate delivery system of claim 17 including
said valve control means adapted to impose one of two voltages across said valves with each voltage placing said valves in one of two said positions.

19. The renal dialysis concentrate delivery system of claim 18 including said valve control means including a manually operable electrical switch.

20. The renal dialysis concentrate delivery system of claim 19 including said valve control means including stepdown transformer means, rectifier means and relay means.

21. The renal dialysis concentrate delivery system of claim 20 including
lamp means responsive to the positions of said valves to provide a visual indication as to which said concentrate reservoir is in use.

22. The renal dialysis concentrate delivery system of claim 1 including first container means for providing additional concentrate receiving capacity in communication with said third supply conduit means.

23. The renal dialysis concentrate delivery system of claim 22 including second container means for providing additional concentrate receiving capacity in communication with said return conduit means.

24. The renal dialysis concentrate delivery system of claim 22 including
relief valve means for permitting flow of concentrate through said return conduit means to a said concentrate reservoir when concentrate pressure in the supply system exceeds a predetermined level.

25. The renal dialysis concentrate delivery system of claim 1 including said third supply conduit means including a supply header and feeder tubes connected at one end to said supply header and having free ends adapted to be connected to a renal dialysis machine, and check valve means in said feeder tubes.

26. The renal dialysis concentrate delivery system of claim 1 including said pump being an occlusion pump.

27. The renal dialysis concentrate delivery system of claim 1 including
an air detector disposed in communication with said supply conduit means, and
signal means responsive to the presence of greater than a predetermined quantity of air or gas in said air detector means to emit a signal.

28. The renal dialysis concentrate delivery system of claim 27 including
said air detector including photocell means.

29. The renal dialysis concentrate delivery system of claim 27 including
pump shutoff means responsive to a signal from signal means to shut off the concentrate pump when the quantity of air or gas detected exceeds said predetermined quantity 30. The renal dialysis concentrate delivery system of claim 1 including
alarm means for indicating pump shutoff for reasons other than shutting off the entire system.

* * * * *